US012642328B2

(12) United States Patent (10) Patent No.: US 12,642,328 B2
Kormann et al. (45) Date of Patent: Jun. 2, 2026

(54) CLOTHING ITEM COMPRISING SPIDER SILK

(71) Applicant: adidas AG, Herzogenaurach (DE)

(72) Inventors: Marco Kormann, Fürth (DE); James Tarrier, Nuremberg (DE); Brian Hoying, Herzogenaurach (DE); Dai Jun, Guangzhou (CN)

(73) Assignee: adidas AG, Herzogenaurach (DE)

( * ) Notice: Subject to any disclaimer, the term of this patent is extended or adjusted under 35 U.S.C. 154(b) by 0 days.

(21) Appl. No.: 15/813,987

(22) Filed: Nov. 15, 2017

(65) Prior Publication Data

US 2018/0132487 A1 May 17, 2018

(30) Foreign Application Priority Data

Nov. 16, 2016 (DE) .......................... 102016222480.8

(51) Int. Cl.
 *A43B 1/02* (2022.01)
 *A01N 63/16* (2020.01)
 (Continued)

(52) U.S. Cl.
 CPC ................ *A43B 1/02* (2013.01); *A01N 63/16* (2020.01); *A43B 1/04* (2013.01); *A43B 3/244* (2013.01);
 (Continued)

(58) Field of Classification Search
 CPC ......... Y10T 442/30–3992; Y10T 442/40–494; Y10T 442/50–59; Y10T 442/60–699; Y10T 428/2936; D03D 1/00–08; D03D 3/00–08; D03D 5/00; D03D 7/00; D03D 9/00; D03D 11/00–02; D03D 13/00–008; D03D 15/00–12; D03D 17/00; D03D 19/00; D03D 21/00; D03D 23/00; D03D 25/00–005; D03D 27/00–18;
 (Continued)

(56) References Cited

U.S. PATENT DOCUMENTS 5,598,615 A * 2/1997 Takada ..................... D04B 1/04
 139/420 R
6,846,545 B2 1/2005 Thomas
 (Continued)

FOREIGN PATENT DOCUMENTS

CN 1711374 12/2005
CN 202208148 5/2012
 (Continued)

OTHER PUBLICATIONS

German Patent Application No. 102016222480.8, Office Action mailed Jun. 18, 2019, 8 pages (English machine translation submitted).
 (Continued)

*Primary Examiner* — Marla D McConnell
*Assistant Examiner* — Kevin Worrell
(74) *Attorney, Agent, or Firm* — Kilpatrick Townsend & Stockton LLP

(57) ABSTRACT

Described are spider silk articles of wear. The article of wear, which may be apparel or shoes, includes an inner surface, wherein the inner surface includes an area including spider silk. The spider silk of the article of wear may be arranged to contact the skin of a wearer when the article of wear is worn.

22 Claims, 7 Drawing Sheets

(51) Int. Cl.

| | |
|---|---|
| *A41D 31/30* | (2019.01) |
| *A43B 1/04* | (2022.01) |
| *A43B 3/24* | (2006.01) |
| *A43B 7/00* | (2006.01) |
| *A43B 17/00* | (2006.01) |
| *A43B 17/10* | (2006.01) |
| *A43B 23/02* | (2006.01) |
| *A43B 23/07* | (2006.01) |
| *C07K 14/435* | (2006.01) |
| *D02G 3/02* | (2006.01) |
| *D03D 1/00* | (2006.01) |
| *D03D 15/233* | (2021.01) |
| *D04B 1/12* | (2006.01) |

(52) U.S. Cl.
CPC ............ *A43B 17/003* (2013.01); *A43B 17/10* (2013.01); *A43B 23/0205* (2013.01); *A43B 23/0235* (2013.01); *A43B 23/07* (2013.01); *C07K 14/43518* (2013.01); *D02G 3/02* (2013.01); *D03D 1/00* (2013.01); *D03D 15/235* (2021.01); *D04B 1/12* (2013.01); *A41D 31/30* (2019.02); *A41D 2400/36* (2013.01); *A41D 2500/10* (2013.01); *A41D 2500/20* (2013.01); *A41D 2500/30* (2013.01); *A43B 7/00* (2013.01); *D10B 2211/04* (2013.01); *D10B 2401/041* (2013.01); *D10B 2401/063* (2013.01); *D10B 2401/13* (2013.01); *D10B 2403/0114* (2013.01); *D10B 2403/032* (2013.01); *D10B 2403/0332* (2013.01); *D10B 2501/043* (2013.01)

(58) Field of Classification Search
CPC ...... D03D 2700/00–90; A43B 1/02–04; A43B 23/26; A43B 23/00–30; A43B 3/06; A43B 5/0488–049; A43B 17/003–006; D02G 3/00–20; D02G 1/00–205; A41D 2400/36
USPC ............... 442/181–303, 304–319, 320–326, 442/327–417, 209–216; 57/207, 57/210–235; 428/36.3, 377
See application file for complete search history.

(56) References Cited

U.S. PATENT DOCUMENTS

| | | | | |
|---|---|---|---|---|
| 7,291,003 | B1 * | 11/2007 | Okandan | D01D 4/02 |
| | | | | 425/131.5 |
| 7,587,841 | B2 | 9/2009 | Culpepper et al. | |
| 7,868,146 | B2 | 1/2011 | Scheibel et al. | |
| 8,097,583 | B2 | 1/2012 | Scheibel et al. | |
| 8,372,436 | B2 | 2/2013 | Hermanson et al. | |
| 9,074,302 | B2 | 7/2015 | Lo et al. | |
| 2003/0041364 | A1 | 3/2003 | Donaldson | |
| 2003/0201560 | A1 | 10/2003 | Vollrath et al. | |
| 2005/0054830 | A1 * | 3/2005 | Islam | D01F 4/02 |
| | | | | 530/353 |
| 2006/0112595 | A1 * | 6/2006 | Vattes | A43B 7/1464 |
| | | | | 36/55 |
| 2006/0165836 | A1 | 7/2006 | Vollrath et al. | |
| 2008/0000106 | A1 * | 1/2008 | Culpepper | A43B 23/17 |
| | | | | 36/89 |
| 2008/0176473 | A1 * | 7/2008 | Wang | D04B 1/18 |
| | | | | 442/329 |
| 2010/0015430 | A1 * | 1/2010 | Hartmann | B32B 27/08 |
| | | | | 428/323 |
| 2015/0056256 | A1 | 2/2015 | Essaidi | |
| 2015/0071978 | A1 * | 3/2015 | Chang | A61N 2/06 |
| | | | | 424/402 |
| 2015/0174256 | A1 * | 6/2015 | Kaplan | A43B 1/02 |
| | | | | 264/28 |
| 2015/0183841 | A1 * | 7/2015 | Lo | A61L 27/52 |
| | | | | 264/164 |
| 2015/0320136 | A1 * | 11/2015 | Dua | D04B 1/16 |
| | | | | 66/170 |
| 2016/0106160 | A1 | 4/2016 | Carneiro | |
| 2016/0222579 | A1 * | 8/2016 | Altman | A61K 8/64 |
| 2016/0250831 | A1 * | 9/2016 | Gladish | C07K 14/43518 |
| | | | | 428/137 |
| 2016/0281294 | A1 | 9/2016 | Altman et al. | |
| 2016/0286898 | A1 * | 10/2016 | Manz | A43B 23/0245 |
| 2016/0298265 | A1 | 10/2016 | Lewis et al. | |
| 2017/0233536 | A1 * | 8/2017 | Purcell | B32B 23/10 |
| | | | | 8/115.6 |
| 2017/0245581 | A1 * | 8/2017 | McFarland, II | D04B 1/24 |
| 2018/0216260 | A1 * | 8/2018 | Breslauer | C07K 14/43518 |

FOREIGN PATENT DOCUMENTS

| | | |
|---|---|---|
| CN | 105829091 A | 8/2016 |
| CN | 205409708 | 8/2016 |
| CN | 205416602 | 8/2016 |
| CN | 106564248 | 4/2017 |
| EP | 2547810 | 1/2013 |
| JP | 6065172 | 4/1985 |
| JP | 09119033 | 5/1997 |
| JP | H10103 | 1/1998 |
| JP | 2006176911 | 7/2006 |
| JP | 2013512773 | 4/2013 |
| WO | 02059412 | 8/2002 |
| WO | 2008083908 | 7/2008 |
| WO | 2011069643 | 6/2011 |
| WO | 2012164080 | 12/2012 |
| WO | 2013065650 | 5/2013 |
| WO | 2014037453 | 3/2014 |
| WO | 2015061079 | 4/2015 |
| WO | 2016028667 | 2/2016 |
| WO | 2016164923 | 10/2016 |
| WO | 2018087239 | 5/2018 |

OTHER PUBLICATIONS

German Patent Application No. 102016222480.8, Office Action mailed May 23, 2017, 7 pages (No English translation available. A summary of the Office Action is provided in the Transmittal Letter submitted herewith).

Japanese Patent Application No. 2017-219705, Office Action mailed Jan. 8, 2019, 8 pages (English translation submitted).

European Patent Application No. 17201986.1, Extended Search Report mailed Apr. 6, 2018, 7 pages.

Japanese Application No. JP 2017219705, "Office Action", Aug. 13, 2019, 6 pages (3 pages of translation and 3 pages of Original document).

Chinese Patent Application No. 201711127883.2, Office Action, Dec. 30, 2019, 13 pages (English machine translation provided).

Chinese Patent Application No. 201711127883.2, Office Action, Jul. 17, 2020, 13 pages (English machine translation provided).

Japanese Patent Application No. 2017-219705 , Office Action mailed Apr. 7, 2020, 6 pages (English machine translation provided).

German Patent Application No. 102016222480.8, Opposition filed Nov. 11, 2020, 113 pages (English machine translation provided).

European Patent Application No. 17201986.1, Third Party Observations filed Dec. 22, 2020, 36 pages.

Chinese Patent Application No. 201711127883.2, Office Action mailed Apr. 19, 2021, 12 pages (English machine translation provided).

European Patent Application No. 17201986.1, Office Action mailed Mar. 24, 2021, 9 pages.

Japanese Patent Application No. 2017-219705, Office Action mailed Apr. 6, 2021, 7 pages (English machine translation provided).

Japanese Patent Application No. 2017-219705, Third Party Submission mailed Dec. 9, 2020, 21 pages (English machine translation provided).

(56)                    References Cited

OTHER PUBLICATIONS

Kiseleva et al., "Recent Advances in Development of Functional Spider Silk-Based Hybrid Materials", Frontiers in Chemistry, vol. 8, Article 554, Jun. 30, 2020, 20 pages.
Office Action, European Patent Application No. 17201986.1, Oct. 17, 2022, 6 pages.
Office Action, European Patent Application No. 17201986.1, Jun. 12, 2023, 4 pages.

\* cited by examiner

FIG 4A         FIG 4B         FIG 4C
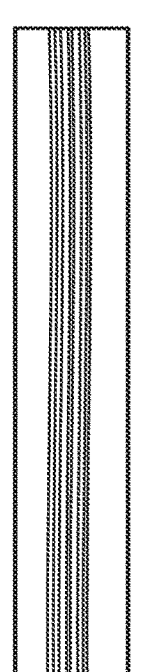 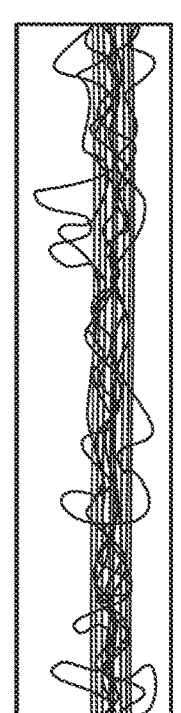 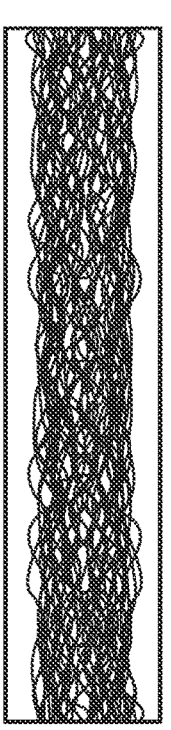
FIG 5A
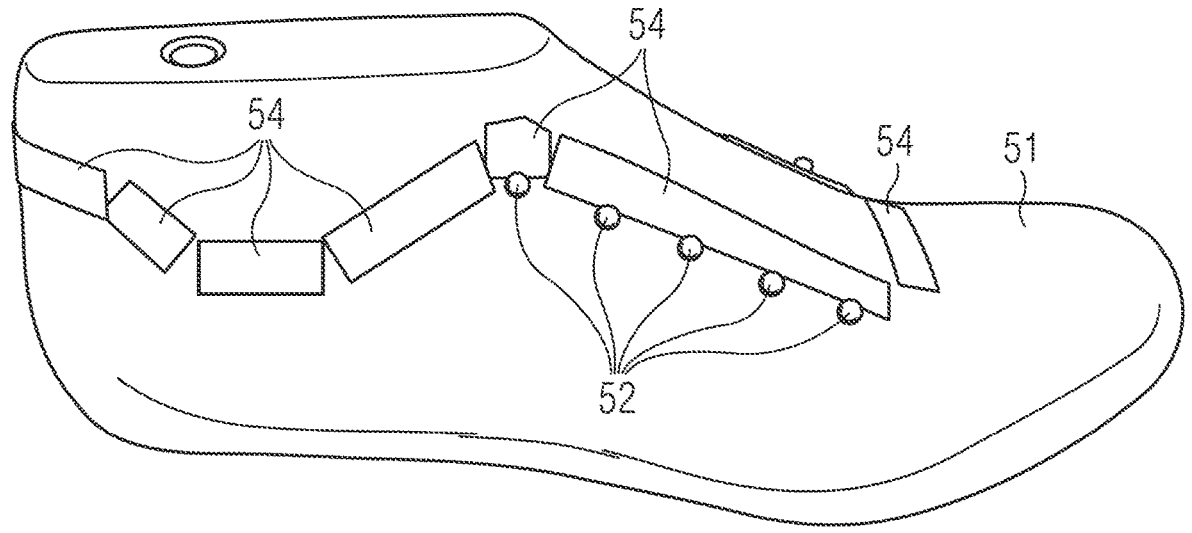

CLOTHING ITEM COMPRISING SPIDER SILK

CROSS REFERENCE TO RELATED APPLICATION

This application is related to and claims priority benefits from German Patent Application No. DE 10 2016 222 480.8, filed on Nov. 16, 2016, entitled APPAREL OR SHOE COMPRISING SPIDER SILK ("the '480.8 application"). The '480.8 application is hereby incorporated herein in its entirety by this reference.

FIELD OF THE INVENTION

The present invention relates to an article of wear, which may be an apparel or shoe, comprising spider silk.

BACKGROUND

Apparel or shoes tend to develop smells because of the development of skin fungi. This is especially true for apparel or shoes made to a large extent from synthetic materials due to the structure of the fibers used. The problem is aggravated with sports apparel or shoes which are subject to sweat when wearing the apparel or shoe during sports activities.

Antibacterial materials such as silver may mitigate the above-mentioned problem. However, some bacteria are beneficial to the human body and even necessary to maintain a healthy skin flora. Therefore, such antibacterial materials may cause more harm than benefit because they tend to kill useful bacteria as well.

According to U.S. Pat. No. 7,587,841 B2, a shoe is provided with an ankle support member to reduce the risk of ankle injury. The ankle support member is a stiff resilient piece of bendable sheet material including a base portion, and a plurality of lateral and medial strips which are inclined upwards and backwards. The ankle support member is bound together with artificial spider web silk for additional strength and flexibility. However, this document neither mentions the technical problem mentioned above nor provides a solution.

It is therefore the objective of the present invention to provide an article of wear, which overcomes or at least reduces the problem of odor formation, in particular with an apparel or shoe for sports applications.

SUMMARY

The terms "invention," "the invention," "this invention" and "the present invention" used in this patent are intended to refer broadly to all of the subject matter of this patent and the patent claims below. Statements containing these terms should be understood not to limit the subject matter described herein or to limit the meaning or scope of the patent claims below. Embodiments of the invention covered by this patent are defined by the claims below, not this summary. This summary is a high-level overview of various embodiments of the invention and introduces some of the concepts that are further described in the Detailed Description section below. This summary is not intended to identify key or essential features of the claimed subject matter, nor is it intended to be used in isolation to determine the scope of the claimed subject matter. The subject matter should be understood by reference to appropriate portions of the entire specification of this patent, any or all drawings and each claim.

According to certain embodiments of the present invention, an article of wear comprises an inner surface, wherein the inner surface comprises an area comprising spider silk.

In some embodiments, the spider silk is arranged to contact the skin of a wearer when the article of wear is worn.

In certain embodiments, the area comprises a first yarn comprising spider silk.

At least a portion of the inner surface, in some embodiments, is formed by a first textile comprising the area.

In certain embodiments, the first textile comprises a first yarn comprising spider silk.

The first textile, in some embodiments, has been shrunk by exposing it to water before it has been incorporated into the article of wear.

In certain embodiments, the first yarn has been shrunk before it is used to form the first textile.

In some embodiments, the first yarn has been shrunk by having it run through a water bath.

In certain embodiments, the first yarn comprises substantially only spider silk.

The first yarn, in certain embodiments, comprises a second material different than spider silk.

In some embodiments, the spider silk and the second material are co-extruded.

The first textile, in some embodiments, comprises a second yarn made from a different material than spider silk.

In certain embodiments, the first yarn is texturized.

In some embodiments, the first textile is at least one of a knitted textile, a woven textile, and a non-woven textile.

The area of the inner surface, in certain embodiments, comprises a coating comprising spider silk.

In some embodiments, the inner surface is a portion of an inner lining.

The article of wear, in some embodiments, further comprising an outer surface comprising spider silk.

In certain embodiments, at least a portion of the outer surface is formed by a second textile comprising spider silk.

The second textile, in some embodiments, comprises a third yarn comprising spider silk.

The second textile, in certain embodiments, comprises at least one of a different knit structure and a different yarn structure compared to the first textile.

In some embodiments, the article of wear further comprising a plurality of layers comprising spider silk.

In certain embodiments, the article of wear comprises a shoe further comprising a shoe upper, wherein the inner surface is a portion of the shoe upper.

In certain embodiments, the article of wear comprises an apparel wherein the area is arranged in an armpit region of the apparel.

According to certain embodiments of the present invention, a method of manufacturing a article of wear comprising: forming an inner surface of the article of wear; and forming an area of the inner surface with spider silk.

BRIEF DESCRIPTION OF THE DRAWINGS

In the following detailed description, embodiments of the invention are described referring to the following figures:

FIGS. 4A, 4B, and 4C are diagrams illustrating a process of texturizing spider silk yarn for a shoe according to certain embodiments of the present invention.

FIGS. 5A, 5B, and 5C are diagrams illustrating a process of steaming and shrinking a three-dimensional shoe upper for a shoe according to certain embodiments of the present invention.

BRIEF DESCRIPTION

Figure 1A:
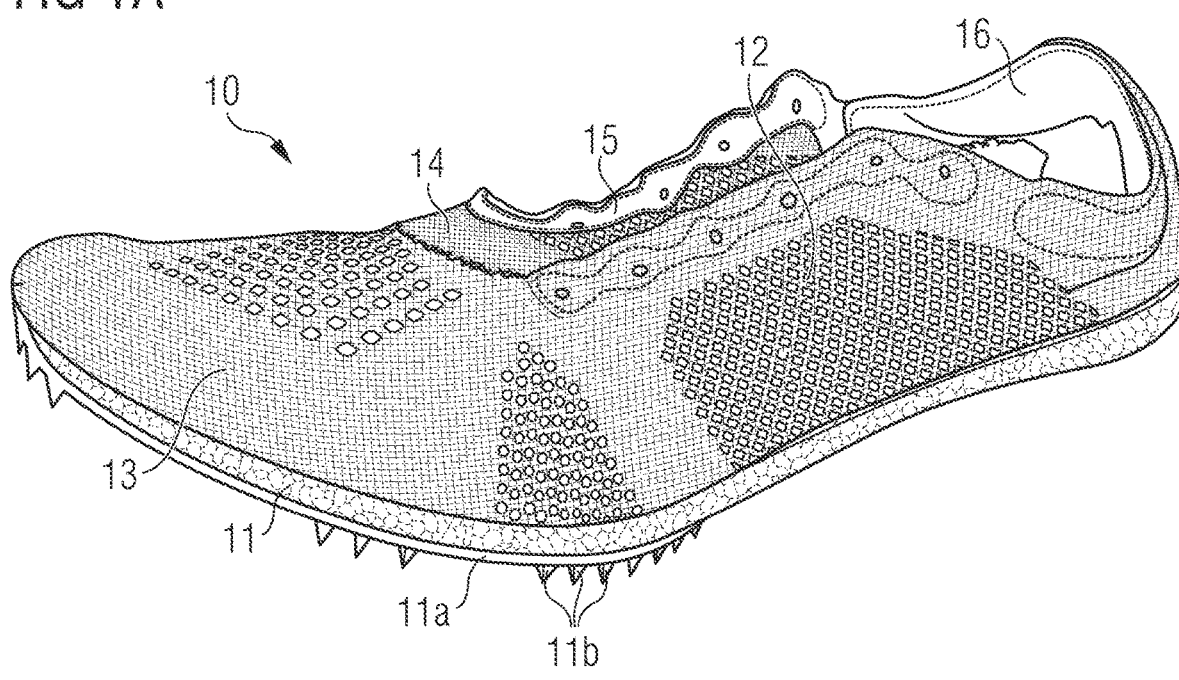
FIG. 1A is a lateral side view of a shoe according to certain embodiments of the present invention.

The objective mentioned above is met by an article of wear, which may be apparel or shoes, comprising an inner surface, wherein the inner surface comprises an area comprising spider silk.

An inner surface in the context of the present invention is understood as a surface adapted to face a wearer's skin.

Spider silk in the context of the present invention is understood as any natural or synthetic material comprising spider silk or spider silk-like proteins. Thus, spider silk in the context of the present invention may either be produced by spiders or synthetic processes which aim to synthesize the properties of natural spider silk. Suitable methods to obtain synthetic spider silk yarns or threads are, for example, described in WO2014037453 A1, U.S. Pat. Nos. 7,868,146, 8,097,583, 8,372,436 and EP2547810 A1.

The inventors of the present invention have found that providing an inner surface of an article of wear with spider silk may reduce the formation of odor, especially for sports apparel or shoes. This is due to the antibacterial effect of spider silk. At the same time, spider silk does not kill all bacteria which populates human skin and helps to maintain a base population of those bacteria which are beneficial to the skin flora. Furthermore, due to its excellent tensile strength, spider silk is able to withstand the forces which are caused by movements of the wearer. This aspect is especially important for sports apparel or shoes. Furthermore, spider silk has a high degree of abrasion resistance. Such resistance may be explained by its filaments having a high tensile strength, such that more force is required to break the filaments. Hence, spider silk is able to fulfill its odor reducing effect over a long period of time.

According to the invention, the spider silk is located in an area of an inner surface of an article of wear. An inner surface of the article of wear is understood as a surface that is adapted to face a wearer's skin when the article of wear is worn in contrast to an outer surface, which would not face a wearer's skin, when the article of wear is worn. This does not necessarily mean that the spider silk directly contacts a wearer's skin. For example, in the case of an apparel such as a tracksuit, sports jacket, shorts, etc. the wearer may wear underwear or another garment, such that the spider silk comes into contact with the underwear or the other garment. In the case of a shoe, the wearer may wear socks, such that the spider silk comes into contact with the socks.

In certain embodiments of the present invention, the spider silk comes in direct contact with the wearer's skin. For example, in case of an apparel, such as underwear, a jersey, a swim suit, a t-shirt, etc., the spider silk may be located at an inner surface of such apparel and may directly contact the wearer's skin. In the case of shoes, the shoes may be worn without socks, which is the case with sprinting shoes, and the spider silk may directly contact the wearer's skin. Thus, the spider silk may be arranged in the article of wear according to the invention to contact the skin of a wearer when the article of wear is worn.

Furthermore, in the case of shoes, the area of the inner surface comprising spider silk may be located at the shoe upper, the insole or both. Generally, the area comprising spider silk may be located at specific locations and may be used to locally increase the strength while having a high resistance (high elongation before break).

Furthermore, spider silk is a material which is strong and has a high elongation before breakage but is also easy to color because it is protein-based. Additionally, spider silk has a high UV-resistance. Other elastic fibers in the industry are not easy to color, such as the Dyneema® fibers, and/or are not resistant to UV, such as Kevlar®.

Furthermore, spider silk is highly moisture absorbent. It can therefore be used in applications where sweat management and/or a cooling effect is sought, be it in apparel or shoes. The spider silk may provide such functions in combination with its other characteristics described herein.

A second area of the shoe or textile may be water repellent. Thus, the area with the spider silk could provide a bacteriostatic and moisture absorbent effect, while the second area could prevent or at least reduce moisture from entering the shoe or apparel. Thus the moisture of the article of wear, and more particularly the sweat of the wearer, may be better managed. In some embodiments it may help to guide and better evaporate sweat. The second water repellent area may overlap at least partially the first area comprising spider silk. Thus, different functions would form in different layers of the article of wear. Besides, a first yarn comprising spider silk may be woven or knit together with a water repellent yarn. In this way, the moisture absorption level may be varied in different areas of the article of wear, for example by varying a proportion of the first yarn.

The mentioned area may comprise a first yarn comprising spider silk. For example, this yarn may be embroidered on a base layer such as leather. In other embodiments, the first yarn may be used to form a textile placed in said area.

At least a portion of the inner surface of the article of wear according to the invention may be formed by a first textile comprising the area. The first textile may comprise a first yarn comprising spider silk. The textile may be formed of 100% spider silk yarn, or may only contain a percentage inferior to 100% and be combined with yarns of different material, whether natural, synthetic or biomimetic. For example spider silk yarns may be used in a knit textile in combination with polyester yarns.

In particular, the textile may be formed of 30% to 100% spider silk, more particularly of 40% to 100% spider silk. Generally, the amount of spider silk may depend on the particular application and may be 50% to 100% when close to a wearer's skin and 10% to 75% for tenacity purposes when farther away from the skin, for example between 10% and 65% for an outer layer of an article of wear.

The spider silk textile may be formed by weaving, knitting, embroidering yarns of spider silk together or with other yarns of different materials, or forming a non-woven textile with fibers of spider silk.

The spider silk yarn may also be embroidered on a base layer. A base layer may be of any material, for example textile, leather, non-woven, polymer sheet, etc. In some embodiments of the invention, the spider silk yarn may be embroidered in specific locations of the article of wear.

The spider silk yarn may be used in a conventional knitting machine with no or very few adjustments and be knitted together with yarns of other materials. In particular, there is no need to change the parameters of the machine to account for the high strength/elasticity of the material. Thus, only small adjustments to the machine are needed, such as speed of the machine and yarn tension. This is different from other fibers such as Kevlar® or Dyneema® that cannot be knit. Due to the high elongation before breakage, a knitting pattern may be used that puts a high tension on the yarn. This allows creating stiff knit textiles that may be integrated in shoe uppers to provide good support such as in lateral support in lateral sports. Also, a textile comprising spider silk according to the invention may comprise spider silk yarns of different deniers and/or thickness (diameter). The yarns may also have different cross-section shapes.

Generally, a spider silk yarn or thread may be used in a textile in particular for a piece of apparel or a shoe, with an increased elasticity and a high strength. In particular, it has a very high elongation at breakage while maintaining its strength. Spider silk is very strong and very elastic compared to Dyneema® and Kevlar®.

The first textile may have been shrunk by exposing it to water before it has been incorporated into the article of wear. A spider silk textile (in particular knit) may shrink with a high shrinkage ratio when first exposed to water. Thereby a very stiff knit textile may be obtained whereby the spider silk is first knitted into a knit textile which is then made to shrink.

The invention also envisions a method of manufacturing an article of wear, which may be a piece of apparel or shoe, in which: (a.) a textile is knitted with at least one yarn comprising spider silk, and (b.) the textile is shrunk. The textile may be shrunk by contact with liquid water or steam. The result is a very stiff knit textile with very small sizes of knit loops. The knit loops "lock" to form a high stiffness knit. That can, for example, be beneficial in a sprinting shoe which needs to be stiff and tight on the foot, while being worn with bare feet. Due to the usage of spider silk according to the invention, the inner surface of the sprinting shoe is both bacteriostatic and provides for a comfortable skin feel.

The textile may be shrunk and then used to create the piece of apparel or shoe (in particular a shoe upper). Thus, according to this first alternative, spider silk yarn (e.g. the first yarn) is used to form a textile (e.g. the first textile), for example by knitting. Then, the textile is shrunk before using it to form the finished product (e.g. an apparel or shoe). For example, in the case of a shoe, the shoe upper is cut in the textile and then used to form the shoe. Alternatively or additionally, at least one layer of the insole may be cut from the spider silk textile with this layer being placed on the top portion of the insole (facing the inside of the shoe).

Alternatively or in combination to the above option, the first yarn may be exposed to water before being used to form a textile. In some embodiments, the yarn may have been shrunk before it is used to form the first textile. In this case, the pre-shrunk spider silk yarn is used to form the first textile which results in a very stiff and durable textile. This technique may be combined with the above technique, i.e. the finished textile may additionally be exposed to water before it is used to manufacture the article of wear. The first yarn may have been shrunk by having it run through a water bath.

Alternatively or in combination the textile may be used to create the piece of apparel or shoe and then shrunk to size—for example a shoe upper may be formed and then shrunk while placed on a last. In some embodiments, a textile may be partially shrunk before being used to form a piece of apparel or shoe, and then be subjected to an additional shrinkage after the piece of apparel or shoe is formed.

In some embodiments however, neither the spider silk yarn nor the textile is shrunk before it is incorporated into the article of wear, but the semi-finished article of wear is exposed to steam and/or water. In this case, the final size (after shrinkage) must of course be considered to obtain an apparel or shoe with the desired size. By this technique, a (partially) stiff and durable article of wear may be obtained.

Since spider silk shrinks mainly when first subjected to steam and/or water, the mentioned options of pre-shrinking the spider silk guarantee that the spider silk in the final product (e.g. an apparel or shoe) will not shrink anymore. In particular, the article of wear comprising spider silk may be exposed to steam. More particularly, a shoe upper may be exposed to steam while on a last. The inventors have found that the shrinking process may be better controlled when using steam instead of water.

The first yarn may comprise essentially only spider silk. Thus, the first textile may comprise essentially only spider silk as well if entirely made from the first yarn. However, in some embodiments, the first textile is manufactured from the first yarn and a second yarn comprising a different material than spider silk. Thus, by mixing spider silk with at least one different material either in the first yarn or by using two different yarns, the properties of the first textile may be tuned. Furthermore, less spider silk is needed compared to forming a textile with pure spider silk yarns.

Generally, a spider silk yarn and a yarn of a different material may be used together to form the area (for example they cross each other in a woven or knit textile). However, in other embodiments, a first area of the textile may comprise the spider silk yarn and a second area of the textile may comprise the yarn of a different material.

When mixing spider silk in the first yarn with another material, the other material may be a natural, synthetic or biomimetic component. Mixing may be achieved by co-extruding or coating for example. Alternatively, fibers may be twisted or mingled, or staple fibers of multiple materials may be combined in a blended staple yarn. A spider silk may for example be applied as a coating on a yarn of a different material, or as wrapping yarns around a yarn of a different material. In an example, the first yarn may comprise spider silk and at least one plastic material. The plastic material may provide an additional function to the yarn and, thus, to the first textile. Examples of such functions are insulation, moisture wicking, water-repellency, additional abrasion resistance, additional stiffness and stability, meltability, color, etc.

The first textile may comprise a second yarn made from a different material than spider silk. In this way, the textile may be provided with an additional function. While the spider silk yarn provides for a bacteriostatic effect, the second yarn may, for example, be moisture wicking to transport sweat away from the skin. The second yarn may, for example, be made from plastic, such as polyester.

The first yarn may be texturized. In this way, the yarn may, for example, be "bulked". This improves the haptic of the yarn by making it softer. Also, such process gives the yarn different mechanical properties. It may in particular improve the yarn's heat resistance, specifically heat created by abrasion or friction with another textile. Also, such yarn may be more insulating as it encloses more air pockets. Such bulking may be obtained by submitting the yarn to air-jet while being formed.

The first textile may be a knit, woven or non-woven. These types of textiles can cost-efficiently be manufactured on appropriate machines. Due to the properties of spider silk, only very few adjustments are needed to process the spider silk.

Also, the spider silk may be added afterwards to the textile, through embroidery or coating for example. The area of the inner surface may comprise a coating comprising spider silk. Thus, the apparel or shoe (such as the shoe upper or insole) may be coated with spider silk proteins so as to benefit from the characteristics of the spider silk, in particular the bacteriostatic effect and comfortable skin feel, at a low cost of production because less spider silk is needed compared to forming a textile with spider silk yarns. Examples of coating may be found in WO 2011069643, which relates to a method for coating an inert or naturally occurring material with a silk polypeptide.

The coating may be a foam, a gel or a non-woven. Examples of how to apply a coating as a foam, gel or non-woven may be found in EP 2615102.

The inner surface may be a portion of an inner lining of the article of wear. In particular, the article of wear (such as the shoe upper and/or the insole) according to the invention may comprise at least one layer comprising spider silk. The benefits of using spider silk for a lining of an apparel or of a shoe upper or insole are that the spider silk is very comfortable and offers a particularly good skin feeling. It is also biocompatible and therefore is non-allergenic, such that the skin is not irritated when the lining comes into direct contact with the skin. It may also be desirable in recovery shoes or apparel as it is a material that is particularly respectful and soft on the skin and the wounds.

As already mentioned, bacteria develop less in textiles including spider silk than in other textiles as spider silk is anti-fouling (bacteriostatic). Therefore, the use of a lining including spider silk in a piece of apparel or in a shoe is particularly beneficial to limit the development of smells due to bacteria or the development of skin fungi. That could reduce in particular the bad odor that is absorbed by clothes when sweating. The spider silk could be used in shoes to be worn with bare foot, insoles, and particular areas of a piece of apparel such as e.g. the arm pits.

The article of wear may further comprise an outer surface comprising spider silk. Spider silk has a very high strength and abrasion resistance and can therefore form the outer layer of a shoe or of a piece of apparel. It may in particular be used in combination with a comfort inner layer as described above.

In some embodiments, at least one area of the piece of apparel or shoe upper comprises only one layer comprising spider silk. Thereby this sole layer forms both the inner surface and outer surface of the piece of apparel or shoe upper.

Alternatively, at least a portion of the outer surface may be formed by a second textile comprising spider silk. The second textile may comprise a third yarn comprising spider silk. In each case, the desirable properties of spider silk would be present on both sides of the article of wear. While on the inside, the bacteriostatic effect would be most important, spider silk on the outside would add to the stiffness, stability and abrasion resistance.

The second textile may comprise a different knit structure and/or yarn structure compared to the first textile. While the knit and/or yarn structure on the inner surface could provide for a comfortable feel, the knit and/or yarn structure on the outer surface could provide for stability, abrasion resistance, etc. In some embodiments, the first yarn used for the first textile on the inner surface is textured as described above. In some embodiments the first textile comprises small knit stitches and the second textile comprises large openings (for example obtained by miss stitches when knitted). The first textile may be placed on the inner surface and the second textile may be placed on the outer surface.

The article of wear may further comprise a plurality of layers comprising spider silk. Besides, at least one layer may be successively peelable. This could provide the possibility to change the aesthetics of a wearable article. It could also avoid having to clean the wearable article when it is dirty. It could also be desirable to have an article looking as if new when the outer layer is removed. It may also improve the hygiene, for example when an internal layer is dirty. Peelable layers may be used for internal surfaces of a piece of apparel or shoe upper, such as a lining for example. It may also be used for external surfaces of a piece of apparel or shoe upper. If it is realized with peelable layers made of biodegradable layers for example including spider silk, the environmental footprint of such products would also remain very low. Such peelable layers may be cut by the wearer or torn along lines of engineered weaknesses in the layer.

The shoe described so far may comprise a shoe upper, wherein the inner surface is a portion of the shoe upper. This can prevent or at least decrease the formation of odor in the shoe thanks to the bacteriostatic properties of spider silk.

The shoe may further comprise a sole structure, wherein the sole structure is separable from the shoe upper. Thus, the area comprising spider silk may be arranged at an inner surface of the shoe upper and the shoe upper may be removed from the sole structure and is biodegradable due to the spider silk. The sole is usually durable and may be used with different or new shoe uppers comprising spider silk. Thereby, the lifetime of the sole may be increased. Indeed, nowadays some wearers often change their shoes because they want to change its aesthetics, and/or because the upper is deteriorated and/or because it is dirty. Since the spider silk is fully biodegradable (it is protein-based) a textile upper made of spider silk has a very low ecological foot print. This applies to a shoe with interchangeable uppers comprising spider silk yarns as well. In the same way, a piece of apparel could comprise an interchangeable layer comprising spider silk yarns. This would make a very sustainable shoe and/or piece of apparel since the durable portions are kept, and the renewed portions are biodegradable.

In case of a piece of apparel the area comprising spider silk may be arranged in an armpit region of the apparel. In this region strength and flexibility is required, as well as moisture absorption and bacteriostatic properties, in particular in some sports such as tennis (service movement). It may also be used in gloves to ensure good protection, and at the same time flexibility and moisture management.

A further aspect of the present invention relates to a method of manufacturing an article of wear as described above, comprising the steps of providing an inner surface of the article of wear, such that it is adapted to face a wearer's skin, and of providing an area of the inner surface with spider silk.

The spider silk used in the context of the present invention may be made sensitive to some specific chemical agent in order to react in a given way to this chemical agent. For example, it may be made to be dissolvable in this specific chemical agent or chemical family. A product containing such spider silk could thus be easily recycled or disposed of in an ecological manner since the spider silk is protein based.

Spider silk in the context of the present invention may be used in a non-woven yarn to form a non-woven textile that may be used in pieces of apparels or shoes in replacement of textiles, or as cushioning pads. Electrospinning may be used to prepare a non-woven yarn comprising spider silk. Such non-woven yarn may also be used as a coating.

The spider silk's properties may be adjusted by modifying the properties of the proteins it is made of, in order to customize its physical and/or chemical properties. For example, it may be reactive to a specific chemical or chemicals family and be programmed to be dissolvable in such chemical, etc.

Generally, spider silk is a material which has a perfect balance between all these different technical functions required in the clothing and shoe industries, and in particular in the sports clothing and sports shoe industry. It is the only material which combines the different features described herein together. Therefore, a shoe upper or a piece of apparel may be formed with only one layer including spider silk, and at the same time exhibiting many functional features simultaneously.

DETAILED DESCRIPTION

The subject matter of embodiments of the present invention is described here with specificity to meet statutory requirements, but this description is not necessarily intended to limit the scope of the claims. The claimed subject matter may be embodied in other ways, may include different elements or steps, and may be used in conjunction with other existing or future technologies. This description should not be interpreted as implying any particular order or arrangement among or between various steps or elements except when the order of individual steps or arrangement of elements is explicitly described.

Figure 1B:
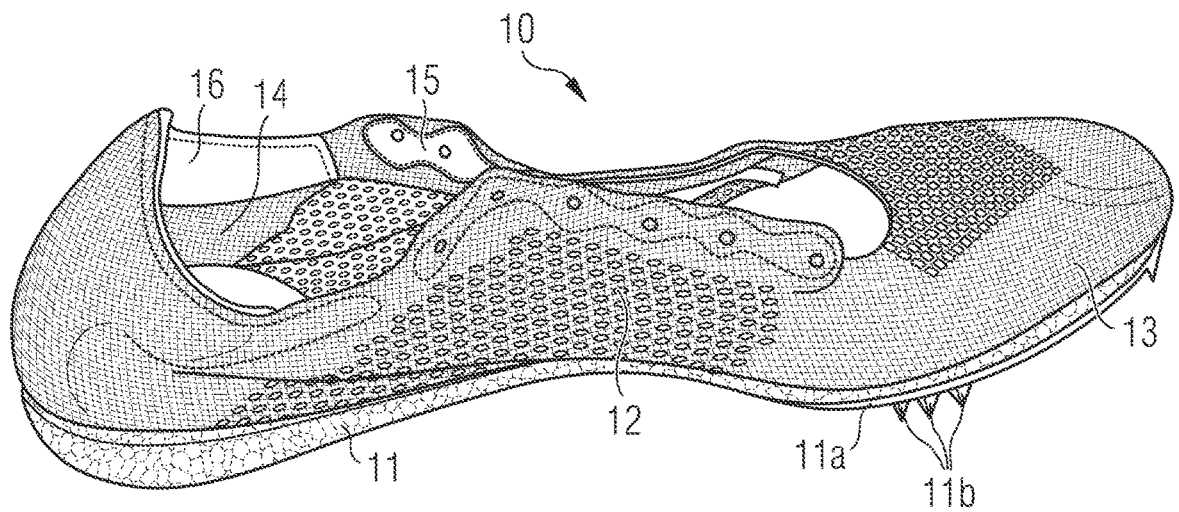
FIG. 1B is a medial side view of the shoe of FIG. 1A.

FIGS. 1A and 1B show exemplary embodiments of a shoe 10 according to the invention, whereby FIG. 1A shows a lateral view and FIG. 1B shows a medial view. However, as described above, the invention may also be embodied in apparel, such as t-shirts, trousers, underwear, jerseys, tracksuits, swim suits, etc. The shoe 10 is a sprinting shoe and comprises a sole structure 11 and a shoe upper 12.

The sole structure 11 comprises an outsole 11a and spikes attached thereto. Three of those spikes are exemplarily denoted with the reference numeral 11b. Attached to the sole 11 is a shoe upper 12. In the example of FIGS. 1A and 1B, the shoe upper 12 is permanently fixed to the sole structure 11. A permanent connection may be achieved by gluing, sewing, welding, and similar techniques.

In the exemplary embodiments of FIGS. 1A and 1B, the upper 12 is a knit upper, i.e. it is made on a knitting machine. More particularly, the upper 12 of FIGS. 1A and 1B has been knitted on a flat knitting machine, according to a partial knitting technique whereby the length of at least one knitting row is different from the length of a subsequent knitting row, so as to give a three-dimensional (non-flat) shape to the knitted upper once out of the knitting machine. Generally, according the invention, an upper may also be made by embroidering, weaving, etc. or may be made from a mesh material or from a non-woven material. The upper 12 in the example of FIGS. 1A and 1B is made from a knitted textile 13. The textile 13 is made from a yarn comprising 100% spider silk. Therefore, the inner surface 14 of the of the shoe upper 12 comprises spider silk as well and is adapted to face the skin of a wearer when the shoe is actually worn. The usage of spider silk reduces the weight of the shoe upper 12 by 20%-30%. The spider silk protein in the exemplary embodiments was made in a bacterial fermentation process by *E. coli*. The protein has then been turned into yarn through a wet spinning process. It should be noted that generally the amount of spider silk in the yarn may be less than 100% as explained above.

In the example of FIGS. 1A and 1B, the shoe upper comprises only one layer on most of its surface. This layer is a knit textile obtained with 100% spider silk. Thereby many inner areas of the shoe upper comprise spider silk, and many outer areas of the shoe upper comprise spider silk.

Thus, in the example of FIGS. 1A and 1B, essentially the entire inner surface of the shoe upper 12 comprises spider silk. However, in other embodiments, spider silk may only be present at a specific area or areas, such as the lateral and/or medial sides, and/or the tongue region and/or the collar region, or combinations of these examples.

In the example of FIGS. 1A and 1B, the shoe upper comprises a plurality of holes which are distinctly larger in diameter than the loop diameter. Those holes are located at the lateral and medial sides, as well as over the toes, and support the circulation of air. The shoe upper 12 comprises some additional components not made from spider silk, such as the reinforcement of the eyelets 15 and the collar pocket 16 containing cushioning material, as well as laces.

The textile 13 was knitted in a 20% larger size and then lasted on a production last. In a next step, the upper was steamed in order to let the yarn shrink in a controlled way so that the shoe upper 12 will then ultimately conform to the size of the last. It should be noted that soaking the shoe upper 12 into water does not always allow sufficient control of the shrinkage.

Alternatively, the knitted textile 13 may be shrunk by exposing it to steam or water before it is incorporated into the shoe 10. Alternatively, the spider silk yarn of the textile 13 may have been shrunk by exposing it to steam or water such as having it run through a water bath before it is used to form the textile 13.

In the example of FIGS. 1A and 1B, the first yarn comprises essentially only spider silk. In some embodiments, a yarn may comprise a mixture of spider silk and a different material. When mixing spider silk in a yarn with another material, the other material may be a natural, synthetic or biomimetic component. Mixing may be achieved by co-extruding or coating for example. Furthermore, the textile 13 may be manufactured from yarn comprising spider silk and a second yarn comprising a different material but no spider silk.

Instead of mixing spider silk with another material in a yarn, the textile 13 may be created, for example, by weaving or knitting with some yarns made of spider silk, and some others made of other materials such as natural fiber based yarns (e.g. cotton, linen, etc.) and/or synthetic fibers (e.g. polyester, nylon, etc.).

In some embodiments, the spider silk yarn may be texturized to add bulk or prepare the yarn for further spinning processing and post processing as will be described with respect to FIGS. 4A, 4B and 4C below. The term "texturize" is often used interchangeably with "crimp".

In the example of FIGS. 1A and 1B, spider silk is present on the inner surface 14 of the shoe upper 12 because the textile 13 from which the shoe upper 12 is made comprises a spider silk yarn. In certain embodiments, the shoe upper may be manufactured from a non-spider silk material, such as polyester or even a natural material such as linen and provide the inner surface of the shoe upper with spider silk. Such a coating may, for example, be applied by spraying, embroidery, etc.

The shoe 10 in the example of FIGS. 1A and 1B does not comprise a lining. However, other embodiments according to the invention may comprise a lining. In that case, an inner surface of the lining may comprise spider silk. In other embodiments, the entire lining is essentially made from spider silk.

In the example of FIGS. 1A and 1B, the outer surface of the shoe upper 12 comprises spider silk as well because the textile 13 from which the shoe upper 12 is formed comprises a spider silk yarn or thread. In other embodiments, the outer surface of the shoe upper may be made from a different textile than the inner surface. This outer textile may comprise a yarn comprising spider silk. In some embodiments, the outer surface of a shoe upper or apparel does not comprise spider silk at all.

If an inner and outer textile is used for a shoe upper, the outer textile may comprise a different knit structure and/or yarn structure compared to the inner textile. Generally, an article of wear according to the invention may further comprise a plurality of layers comprising spider silk.

Figure 2:
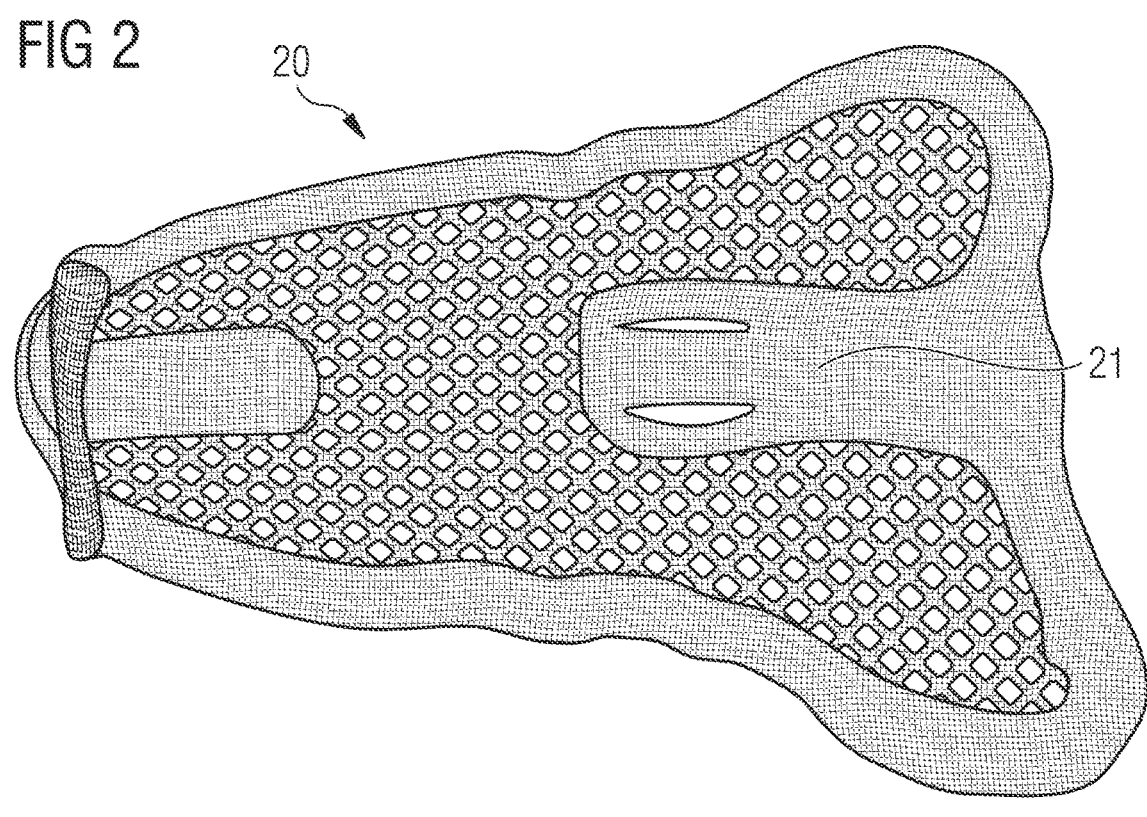
FIG. 2 is a top view of a tongue according to certain embodiments of the present invention which may be used in certain embodiments of the shoe of FIGS. 1A and 1B.

FIG. 2 shows a tongue 20 which may be attached to the exemplary shoe upper 12 of FIGS. 1A and 1B. The tongue 20 is also made from a knitted textile 21 comprising spider silk. The tongue 20 comprises a plurality of holes which are distinctly larger in diameter than the loop diameter of the textile 21 to allow for air circulation.

FIGS. 3A, 3B, 3C and 3D show other embodiments of the present invention, namely a running shoe 10. Just like the shoe 10 of FIGS. 1A and 1B, this shoe 10 comprises a shoe upper 12 attached to sole structure 11 as well. The shoe upper 12 is made from a knitted textile 13. The textile 13 forms a layer which forms most of the surface of the shoe upper 12, more particularly the entire surface of the shoe upper. The knitted textile 13 in the embodiments comprises a first area or portion 31 which makes up the largest portion of the shoe upper 12 and which is made of 100% spider silk. However, in variations of the embodiments, the amount of spider silk in this area 31 may be less than 100%.

The textile 13 comprises a second area or portion 32 comprising the tongue and collar which does not comprise spider silk. However, in a variation of the embodiments, this second area 32 could comprise some amount of spider silk. It is important to note that the percentage of spider silk in the first area 31 is different than in the second area 32.

The second area 32 may comprise a mix of different yarns like for example polyester and elastane. The first portion 31 and the second portion 32 are knitted together.

Figure 3A:
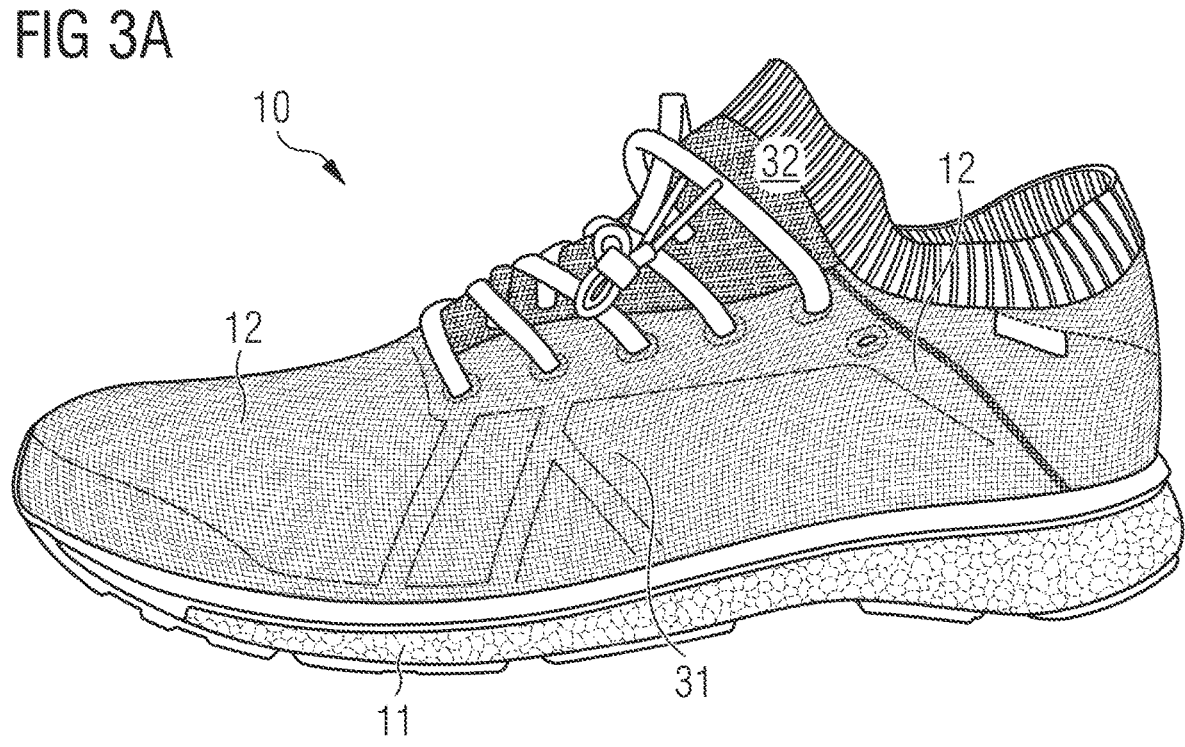
FIG. 3A is a lateral side view of a shoe according to certain embodiments of the present invention.
Figure 3B:
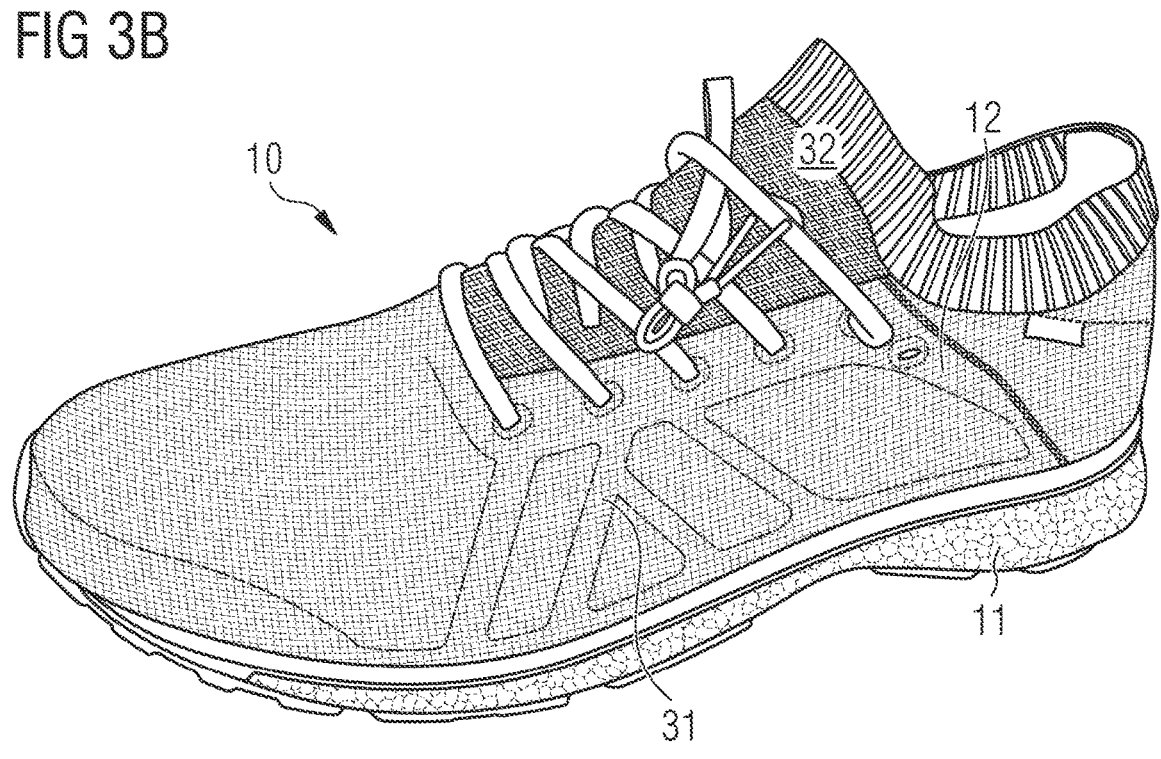
FIG. 3B is a lateral perspective view of the shoe of FIG. 3A.
Figure 3C:
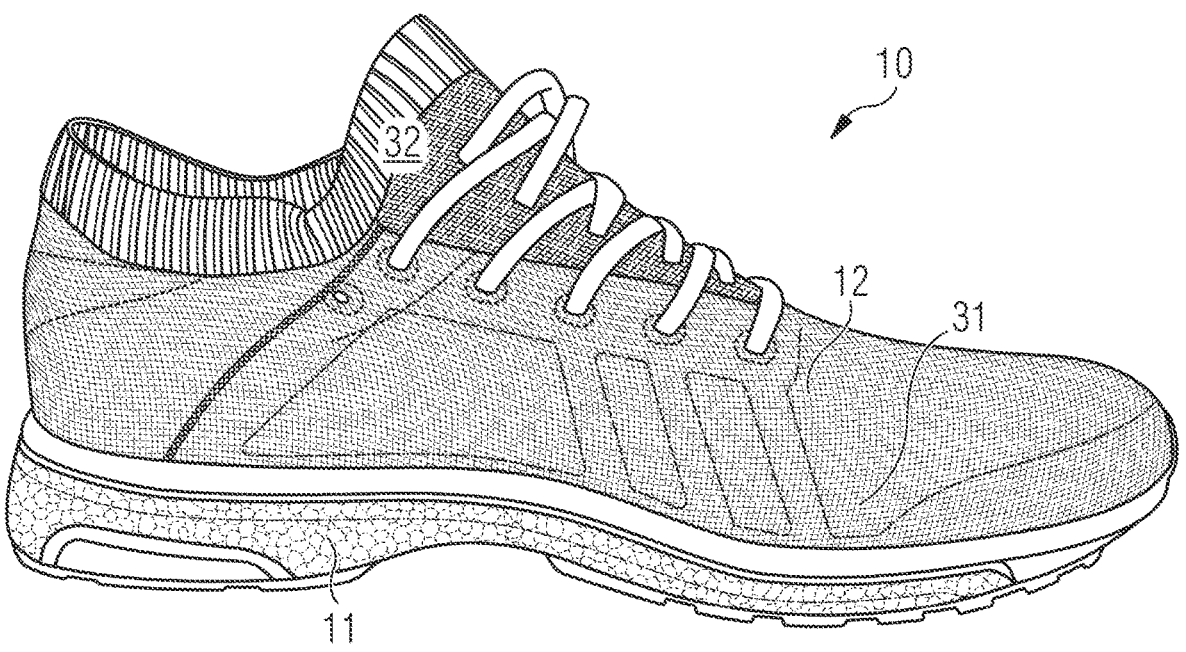
FIG. 3C is a medial side view of the shoe of FIG. 3A.
Figure 3D:
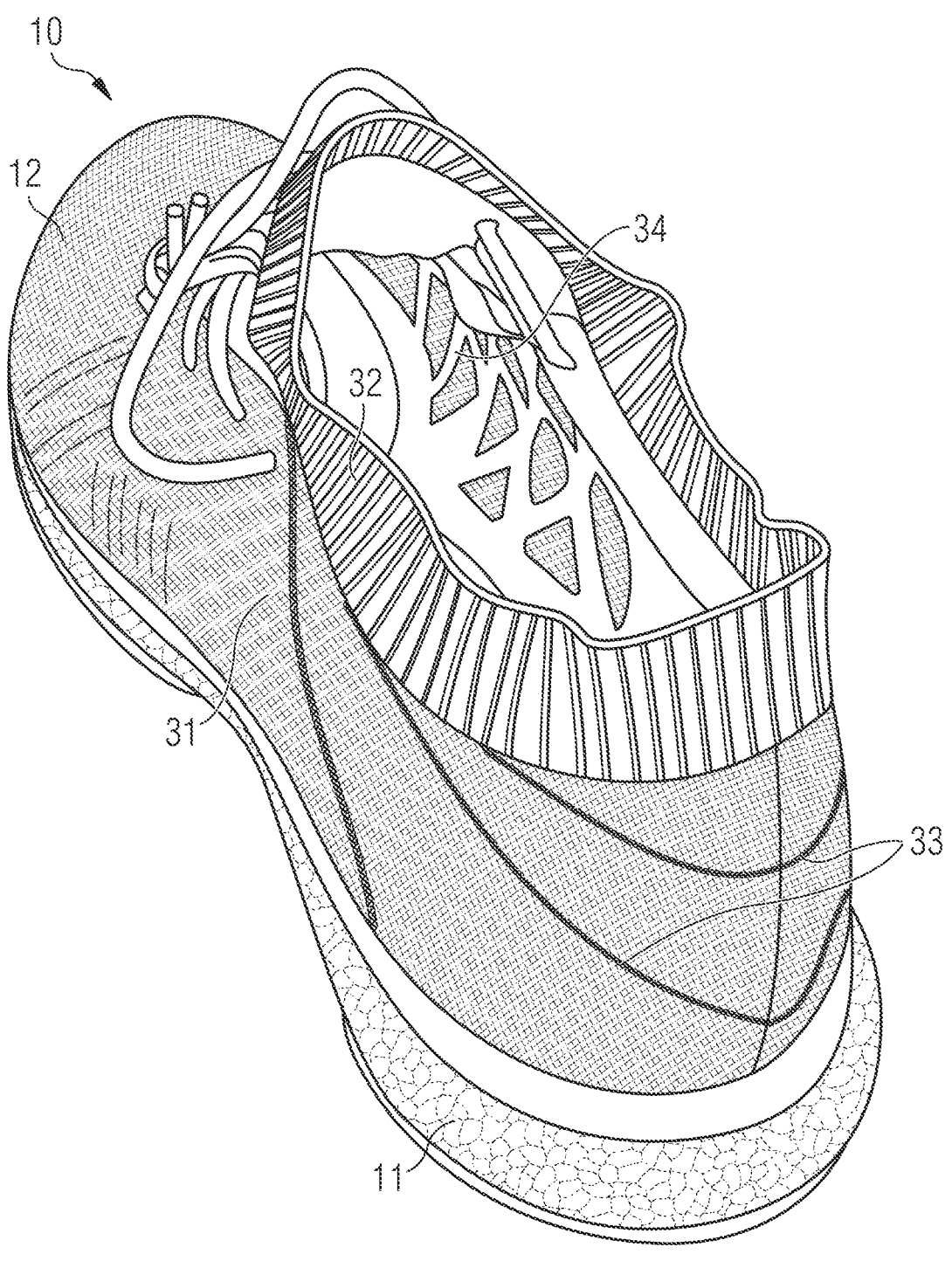
FIG. 3D is a rear perspective view of the shoe of FIG. 3A.

Besides, as may be seen in FIG. 3D, there are lines of partial knitting 33 in the heel area to give the shoe upper 12 a three-dimensional shape on a flat knitting machine.

Furthermore, the shoe upper 12 comprises a webbing 34 to modify locally the elasticity of the shoe upper 12.

FIGS. 4A, 4B and 4C illustrate the process of texturizing spider silk yarn as mentioned above. Generally, yarn may be texturized to add bulk or to prepare yarn for a further spinning process, post processing, knitting, weaving, etc. Texturizing also affects the hand feel of the yarn. Texturizing also affects properties of the yarn such as resistance to abrasion or tensile strength.

FIG. 4A shows a conventional yarn. FIG. 4B shows an air-jet texturized yarn which was treated by an air-jet. FIG. 4C shows a false twist texturized yarn obtained by a higher degree of air-jet treatment—for example treatment of the yarn with an air-jet of higher power and/or at lower running speed of the yarn.

Figure 5B:
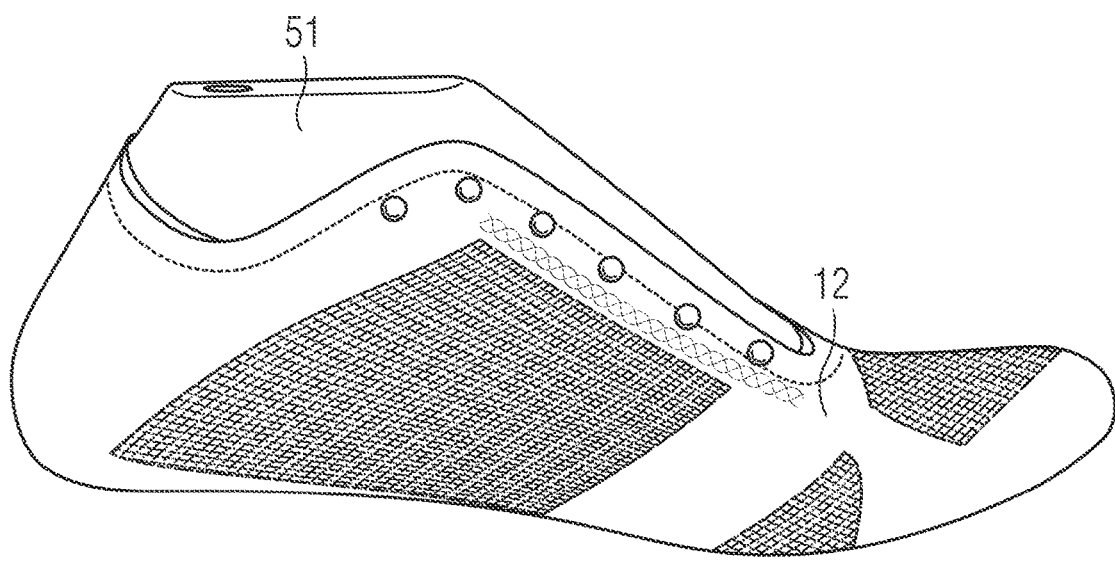
Figure 5C:
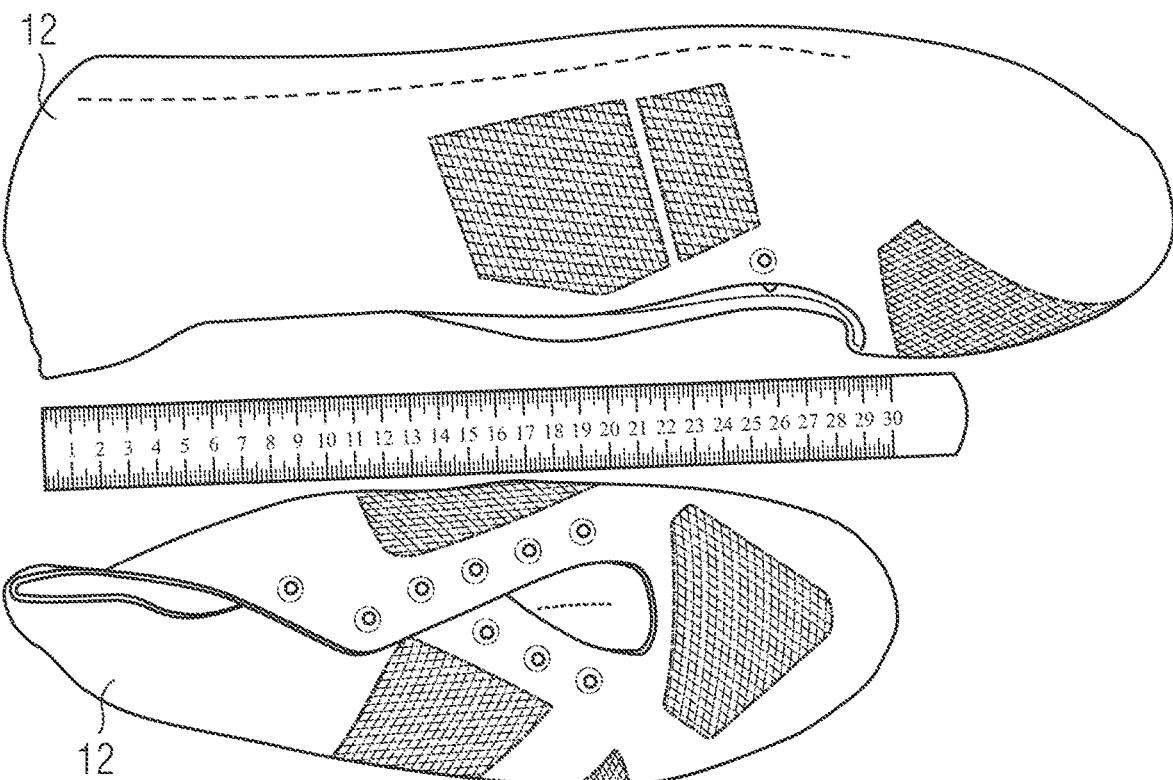

FIGS. 5A, 5B and 5C illustrate the process of steaming and shrinking a shoe upper 12 as mentioned above. In this example, the shoe upper 12 is knitted in 360 degrees as a sock. For the steaming process, the shoe upper 12 is laid on a flat surface, such as a table. A steaming iron is placed above the shoe upper 12 in a distance of about 5 cm, i.e. not touching the shoe upper 12. Steam is gently released on the shoe upper 12 for a short period of time, such as 4-5 seconds, to pre-shrink the shoe upper 12. Thus, in this pre-shrinking step (not shown in FIGS. 5A-5C), steam is applied, but no pressure.

Then, the shoe upper 12 is put on a last 51 which is shown in FIG. 5A without the shoe upper 12. On the last 51, the shoe upper 12 is steamed and ironed until it fits on the last 51. In this second step, steam and pressure is applied, wherein the application of pressure is optional in this step.

As mentioned above, the last 51 is shown in more detail in FIG. 5A and comprises pins 52 for the eyelets of the shoe upper 12. These pins 52 are also used to hold the shoe upper 12 during steaming. The last 51 also comprises strips of hook-and-loop fasteners 54 to hold the upper 12 for positioning while steaming and optionally applying pressure.

It should be noted that the step of pre-shrinking the shoe upper 12 as described above is important because otherwise, the shoe upper 12 would be too big to be placed on the last.

FIG. 5C illustrates the amount of shrinking. The top portion of FIG. 5C shows a shoe upper 12 before shrinking as described above, whereas the lower portion shows the shoe upper 12 after the shrinking process.

Figures 6A, 6B:
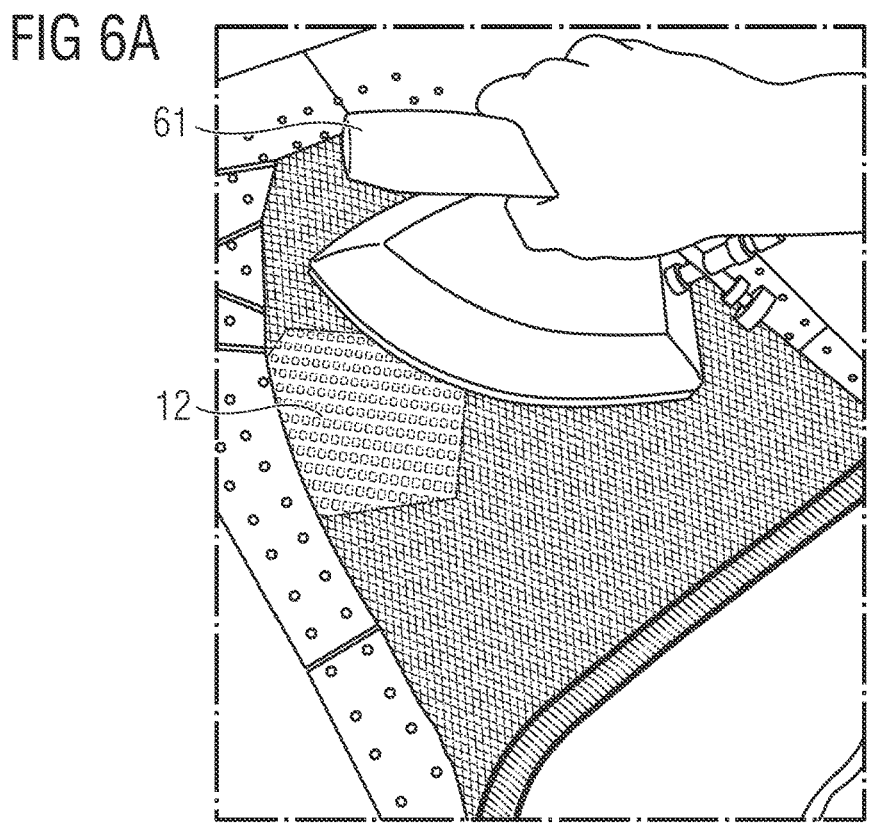
FIGS. 6A and 6B are diagrams illustrating a process of steaming and shrinking a two-dimensional shoe upper for a shoe according to certain embodiments of the present invention.

The shrinking process as described above can also be applied to two-dimensional knitted shoe uppers. The difference is that no last is used as illustrated in FIGS. 6A and 6B. In this case, the shoe upper 12 is also pre-shrunk by placing an iron 61 above the shoe upper 12 without touching it. Then, steam is gently applied. In a second step, the shoe upper 12 is laid flat on a board 62 to apply steam and optionally pressure to shrink the shoe upper 12 to its final size. The board 62 comprises pins like the pins 52 of the last 51. Two of those pins are exemplarily denoted with the reference numeral 63 in FIG. 6B.

In the following, further examples are described to facilitate the understanding of the invention:

Example 1

Apparel or shoe (12) comprising:
an inner surface (14), wherein the inner surface (14) comprises an area (31) comprising spider silk.

Example 2

Apparel or shoe (12) according to the preceding Example 1, wherein the spider silk is arranged to contact the skin of a wearer when the apparel or shoe (12) is worn.

Example 3

Apparel or shoe (12) according to the preceding Example 1, wherein the area (31) comprises a first yarn comprising spider silk.

Example 4

Apparel or shoe (12) according to one of the preceding Examples, wherein at least a portion of the inner surface (14) is formed by a first textile (13) comprising the area (31).

US 12,642,328 B2

13

Example 5

Apparel or shoe (12) according to the preceding Example, wherein the first textile (13) comprises a first yarn comprising spider silk.

Example 6

Apparel or shoe (12) according to the preceding Example, wherein the first textile (13) has been shrunk by exposing it to water before it has been incorporated into the apparel or shoe (12).

Example 7

Apparel or shoe (12) according to the preceding Example 5, wherein the first yarn has been shrunk before it is used to form the first textile (13).

Example 8

Apparel or shoe (12) according to the preceding Example, wherein the first yarn has been shrunk by having it run through a water bath.

Example 9

Apparel or shoe (12) according to the preceding Example, wherein the first yarn comprises essentially only spider silk.

Example 10

Apparel or shoe (12) according to one of the preceding Examples 3 or 5 to 8, wherein the first yarn comprises a second material different than spider silk.

Example 11

Apparel or shoe (12) according to the preceding Example, wherein the spider silk and the second material are co-extruded.

Example 12

Apparel or shoe (12) according to one of the preceding Examples 5 to 11, wherein the first textile comprises a second yarn made from a different material than spider silk.

Example 13

Apparel or shoe (12) according to one of the preceding Examples 3 or 5 to 12, wherein the first yarn is texturized.

Example 14

Apparel or shoe (12) according to one of the preceding Examples 4 to 13, wherein the first textile (13) is a knit, woven or non-woven.

Example 15

Apparel or shoe (12) according to one of the preceding Examples, wherein the area of the inner surface comprises a coating comprising spider silk.

14

Example 16

Apparel or shoe (12) according to one of the preceding Examples, wherein the inner surface (14) is a portion of an inner lining.

Example 17

Apparel or shoe (12) according to one of the preceding Examples, further comprising an outer surface comprising spider silk.

Example 18

Apparel or shoe (12) according to the preceding Example, wherein at least a portion of the outer surface is formed by a second textile comprising spider silk.

Example 19

Apparel or shoe (12) according to the preceding Example, wherein the second textile comprises a third yarn comprising spider silk.

Example 20

Apparel or shoe (12) according to the preceding Example, wherein the second textile comprises a different knit structure and/or yarn structure compared to the first textile.

Example 21

Apparel or shoe (12) according to one of the preceding Examples, further comprising a plurality of layers comprising spider silk.

Example 22

Shoe (12) according to one of the preceding Examples, comprising a shoe upper (12), wherein the inner surface (14) is a portion of the shoe upper (12).

Example 23

Apparel according to one of the preceding Examples 1 to 21, wherein the area is arranged in an armpit region of the apparel.

Example 24

Method of manufacturing an apparel or shoe (12) according to one of the preceding Examples, comprising the steps:
  providing an inner surface (14) of the apparel or shoe (12);
  providing an area of the inner surface (14) with spider silk.

Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

That which is claimed is:

1. A bacteriostatic article of footwear, wherein the bacteriostatic article of footwear comprises:
   an upper comprising an inner surface,
   wherein at least one portion of the inner surface comprises a knitted textile comprising:
      a first yarn comprising a spider silk yarn wrapped around a second yarn of a different material than spider silk;
      a third yarn formed exclusively from at least one material, wherein the at least one material does not include spider silk; and
   wherein the third yarn is positioned at least partially on the inner surface to contact a wearer when the bacteriostatic article of footwear is worn;
   wherein the knitted textile comprises at least 50% and less than 100% spider silk; and
   wherein a first area of the upper comprises the first yarn, the second yarn, and the third yarn and comprises a first ratio of the first yarn to the third yarn and a first moisture absorption level based on the first ratio, and a second area of the upper comprises the first yarn, the second yarn, and the third yarn and comprises a second ratio of the first yarn to the third yarn and a second moisture absorption level based on the second ratio.

2. The bacteriostatic article of footwear according to claim 1, wherein:
   the at least one portion of the inner surface has been shrunk by exposing it to water before it has been incorporated into the bacteriostatic article of footwear;
   the first yarn has been shrunk before it is used to form the at least one portion of the inner surface; or
   the first yarn has been shrunk by having it run through a water bath.

3. The bacteriostatic article of footwear according to claim 1, wherein the upper comprises at least one water repellant portion arranged to at least partially overlap the at least one portion of the inner surface.

4. The bacteriostatic article of footwear according to claim 1, wherein the first yarn comprises substantially only spider silk.

5. The bacteriostatic article of footwear according to claim 1, wherein the first yarn comprises a second material different than spider silk.

6. The bacteriostatic article of footwear according to claim 5, wherein the spider silk and the second material are co-extruded.

7. The bacteriostatic article of footwear according to claim 1, wherein the first yarn is texturized.

8. The bacteriostatic article of footwear according to claim 1, wherein the at least one portion of the inner surface further comprises at least one of a woven textile or a non-woven textile.

9. The bacteriostatic article of footwear according to claim 1, wherein the at least one portion of the inner surface comprises a coating comprising spider silk.

10. The bacteriostatic article of footwear according to claim 1, wherein the knitted textile comprising the first yarn comprising spider silk is arranged exclusively in one or more of a lateral side region of the upper, a medial side region of the upper, a tongue region of the upper, or a collar region of the upper.

11. The bacteriostatic article of footwear according to claim 1, wherein at least one portion of an outer surface of the bacteriostatic article of footwear comprises spider silk.

12. The bacteriostatic article of footwear according to claim 11, wherein the at least one portion of the outer surface comprises a fourth yarn comprising spider silk.

13. The bacteriostatic article of footwear according to claim 11, wherein the at least one portion of the outer surface comprises at least one of a different knit structure or a different yarn structure compared to the at least one portion of the inner surface.

14. The bacteriostatic article of footwear according to claim 1, further comprising a plurality of layers comprising spider silk, wherein at least one of the plurality of layers is removable from the remaining layers of the plurality of layers.

15. The bacteriostatic article of footwear according to claim 1, wherein the bacteriostatic article of footwear comprises a shoe further comprising the upper.

16. The bacteriostatic article of footwear according to claim 1, wherein the at least one material forming the third yarn comprises a moisture wicking material.

17. A bacteriostatic article of footwear comprising:
   an upper comprising an inner surface and an outer surface;
   wherein at least one portion of the inner surface and at least one portion of the outer surface comprises:
      a first yarn comprising a spider silk yarn wrapped around a second yarn of a different material than spider silk; and
      a third yarn formed exclusively from at least one material, wherein the at least one material does not include spider silk; and
      wherein the third yarn is positioned at least partially on the inner surface to contact the skin of a wearer when the bacteriostatic article of footwear is worn;
      wherein the at least one portion of the outer surface comprises 10% to 65% spider silk; and
      wherein a first area of the inner surface comprises the first, second and third yarns and comprises a first ratio of the first yarn to the third yarn and a first moisture absorption level based on the first ratio, and a second area of the inner surface comprises the first, second and third yarns and comprises a second ratio of the first yarn to the third yarn and a second moisture absorption level based on the second ratio.

18. The bacteriostatic article of footwear according to claim 17, wherein the at least one material forming the third yarn comprises a moisture wicking material.

19. The bacteriostatic article of footwear according to claim 17, further comprising a plurality of layers comprising spider silk, wherein at least one of the plurality of layers is removable from the remaining layers of the plurality of layers.

20. The bacteriostatic article of footwear according to claim 17, wherein the upper comprises at least one water repellant portion arranged to at least partially overlap the at least one portion of the inner surface.

21. The bacteriostatic article of footwear according to claim 17, wherein the at least one portion of the inner surface comprises at least 50% and less than 100% spider silk.

22. The bacteriostatic article of footwear according to claim 17, wherein the first yarn comprising spider silk is arranged exclusively in one or more of a lateral side region of the upper, a medial side region of the upper, a tongue region of the upper, or a collar region of the upper.

\* \* \* \* \*